United States Patent [19]

Mulcahy et al.

[11] Patent Number: 4,620,391
[45] Date of Patent: Nov. 4, 1986

[54] METHOD OF PRODUCING SELF-INCOMPATIBLE PLANTS

[76] Inventors: David L. Mulcahy; Gabriella B. Mulcahy, both of 14 Cosby Ave., Amherst, Mass. 01002

[21] Appl. No.: 621,443

[22] Filed: Jun. 18, 1984

[51] Int. Cl.$^4$ ............................................. A01G 1/00
[52] U.S. Cl. .................................... 47/58; 47/DIG. 1
[58] Field of Search ..................... 47/58, 1.41, DIG. 1

[56] References Cited

U.S. PATENT DOCUMENTS

| | | | |
|---|---|---|---|
| 4,102,079 | 7/1978 | Kataoka | 47/58 |
| 4,143,486 | 3/1979 | Maan | 47/58 |
| 4,254,580 | 3/1981 | Ferguson | 47/58 |
| 4,378,655 | 4/1983 | Johnson | 47/58 |
| 4,381,624 | 5/1983 | Lawrence, Jr. et al. | 47/58 |

OTHER PUBLICATIONS

David L. Mulcahy and Gabriella B. Mulcahy, Science 220:1247-1251 (Jun. 17, 1983) "Gametophytic Self-Incompatibility . . . "
David A. Evans et al., Science 221:949-952 (Sep. 2, 1983) Single Gene Mutations in Tomato Plants . . . "
C. M. Rick, "The Potential of Exotic Germplasm . . . " in Plant Improvement and Somatic Cell Genetics, Vasil et al. Eds. 1982.
D. de Nettancourt, Incompatibility in Angiosperms, pp. 192-194 Springer-Verlag, Berlin, New York, 1977.
"Somatic Cell Genetics" in *Genetic Engineering of Plants*, pp. 33-39 (National Academy Press, 1984).
D. deNettancourt et al., *Proc. R. Soc. London, B. 188, 345-360 (1975).*
Stebbins, *American Naturalist*, 91, 337-354 (1957).
Lewis et al., "Unilateral Interspecific Incompatibility in Flowering Plants"in *Heredity*, 12, 233-256 (1958).
Martin, *Genetics*, 60 101-109 (1968).
Martin, *Genetics* 46 1443-1454 (1961).
Martin, *Stain Tech.*, 34, 125-128 (1958).

*Primary Examiner*—Robert E. Bagwill
*Attorney, Agent, or Firm*—Ernest V. Linek; David G. Conlin

[57] ABSTRACT

This invention is directed to the breeding of self-incompatible plants, especially crop plants. In particular, the invention is directed to novel self-incompatable crops and hybrid seeds thereof.

17 Claims, No Drawings

METHOD OF PRODUCING SELF-INCOMPATIBLE PLANTS

BACKGROUND OF THE INVENTION

Self-incompatible plants are plants which set seeds or fruit only if they receive pollen from a different variety of the the same species. For example, a Red Delicious apple tree will not set fruit if the only pollen available to it is Red Delicious pollen. This is the case even if the pollen is from another tree of the same variety. The same situation occurs for MacIntosh apple trees. However, the availability of MacIntosh pollen will result in fruit on Red Delicious trees and vice-versa. Both varieties are thus described as "self-incompatible". Sour cherries, in contrast, are "self-compatible" in that a single individual will set fruit employing its own pollen. Most commercially useful crops are self-compatible, including for example, crops such as sugar beets, tomato, and the cereals; corn, wheat, rice, barley, Self-compatible crops are well known to the skilled artisan.

When seeds are obtained from cross pollenation between different plant varieties, the plants produced are often superior in terms of plant vigor, production and/or disease resistance. Such superiority is known as "hybrid vigor". The advantages of hybrid vigor are so great that 95% of the corn crop grown in the United States is grown from hybrid seed.

While many crops would benefit from hybrid vigor, few possess the characteristics which allow for creating self-incompatability on a commercial scale. One crop wherein self-incompatibility is used in the production of a hybrid is cabbage. See for example, Lawrence, Jr., et al., U.S. Pat. No. 4,381,624, which is incorporated herein by reference.

One approach previously used for producing hybrid plants was, cytoplasmic male sterility. For example, it has been employed to produce hybrid onion seeds. Cytoplasmic male sterility has also been employed in producing hybrid corn; see, Jones, U.S. Pat. No. 2,753,663 and hybrid wheat; see Maan, U.S. Pat. No. 4,143,486. This approach is not without its problems; for example, cytoplasmic male sterility is labor intensive and depending upon the nature of the plant, is often unsuccessful in producing viable hybrid seeds.

Self-incompatibility, as induced in plants using the methods of the present invention is another useful technique for the production of hybrid seeds. As noted above hybrid seeds often produce plants which are superior to other plants. In addition, hybrid seeds permit the sale of genotypes without loss of control over those genotypes since genetic segregation disassembles the genotype at the end of one generation.

Self-incompatibility may be considered either a nuisance or a benefit to a plant breeder depending upon the nature of the crop (seed or vegetation part) and upon the kind of reproduction, vegetative or sexual. The induction of self-incompatibility in a plant can serve three purposes:

1. The large scale production of heterotic $F_1$ hybrids;
2. The suppression of fructification processes in crops where parthenocarpy is not effective and where fruit production is considered to be either a loss of energy or an inhibition of vegetative growth or continued flowering; and
3. The production of seedless or stoneless fruits in orchard species or in crops like pineapple and banana where parthenocarpy is effective. See: D. de Nettancourt, *Incompatibility in Angiosperms*, pp. 192–194, (Springer-Verlag, Berlin, 1977).

G. L. Stebbins, in *American Naturalist*, 91, 337–354 (1957) summarized indications that the direction of evolution is from self-incompatible species to self-compatible species and not the reverse. Included among his evidence is the fact that self-compatibility was derived in historical times and has also been derived in several well documented experimental studies. However, neither in historical times nor in experimental studies has self-incompatibility been created, induced in, or transferred to a self-compatible species. Indeed, Whitehouse, in *Annals of Botany N.S.*, 14, 198–216 (1950) suggested that self-incompatibility may have originated only once, about 120 million years ago, during the evolution of the angiosperms. This suggestion is perhaps somewhat extreme, but some of the foremost investigators of self-incompatibility clearly affirm that the evolution of self-incompatibility is an event of great antiquity and rarity; see also, Lewis and Crowe, *Heredity*, 12 233–256 (1958).

Since the creation of self-incompatibility by botanists or plant breeders has been presumed to be virtually impossible, attempts have been devoted to transferring self-incompatibility from wild species into self-compatible species. These attempts were always unsuccessful. See for example, Mather, *Jour. Genetics*, 45, 2215–235 (1943); Martin, F. W., and *Genetics*, 46, 1443–1454 (1961), *Genetics*, 60 101–109 (1968); and de Nettancourt et al., *Proceedings of the Royal Society of London, B.*, 188, 345–360 (1975). Rick, C. M., in *Plant Improvement and Somatic Cell Genetics*, I. K. Vasil et al., eds. pp. 1–28 (Academia Press, N.Y., 1982) commenting upon an investigation of the interrelationships of several genetic traits and self-incompatibility in several tomato species, wherein the control of critical traits, e.g., stigma exsertion, size of flower, and inflorescence, was found to be polygenic and inherited largely independently of the self incompatibility loci; has stated that considering the complexity of these problems, the prospects at this time do not look bright for exploiting self-incompatibility in this fashion.

According to the classical model of self-incompatibility the reaction is controlled by a single genetic locus. This locus is thought to exist in a very large variety of configurations (alleles). Because pollen grains carry only one half as many chromosomes as do many other cells, each pollen grain carries only a single self-incompatibility allele. The portion of the flower upon which pollen lands (the style) carries two incompatibility alleles in each cell. If the incompatibility allele in the pollen is matched by either of the alleles in the style, the pollen is "incompatible" and will fail to reach an egg. The classical model maintains that this failure results from the liberation of a specific pollen inhibiting molecule, something functionally equivalent to antibodies attacking a pathogen. It must further be noted that the classical model indicates that both incompatibility alleles in the style are expressed.

The heterosis model of the present invention, (see, Mulcahy et al., *Science*, 220 1247–1251 (1983), incorporated herein by reference) states that self incompatibility is determined, not by one, but by several genetic loci. Furthermore, this model does not assume that these loci are particularly unique nor that they are ancient in origin. It suggests that, if pollen and style differ in many of these loci, the pollen tubes grow quickly. If they carry many of the same alleles, then the pollen tubes may grow so slowly that they fail to reach the eggs. The most functional difference between the two models is that the classical is strictly qualitative whereas the alternative model is quantitative.

One immediate consequence of the differences between the two models is that observations which are anomalous according to the classical model become axiomatic under the heterosis model of the present invention. More to the point however, is the fact that, according to the present heterosis model, it is now possible to select for plant breeders to select for increased or decreased tendencies toward self-incompatibility.

SUMMARY OF THE INVENTION

The present invention is directed to a method of selecting plants with tendencies toward self-incompatibility and thereby producing self-incompatible plants. Self-incompatibility is useful in the production of hybrid seeds and also preventing seed formation when seeds or fruits are considered deleterious. The method consists of two basic features:

1. Inbreeding with techniques which largely eliminate pollen tube competition.
2. Using temperatures which are nearly optimal for pollen tube growth through the styles, and then screening and selecting the products of this inbreeding for tendencies toward self-incompatibility.

DETAILED DESCRIPTION

Selecting for self-incompatibility consists of starting with heterozygous genotypes. That is, for those cells which contain two sets of chromosomes, many of the loci will be represented as two different alleles. When pollen grains are produced by the heterozygote many new genetic combinations will be formed as the two parental gene sets are recombined. Some of these combinations are nonviable and these result in reduced pollen viability. When the heterozygotes are self-pollinated or "selfed", some of the pollen types grow through the style quickly, others more slowly. The latter pollen tubes include those with stronger tendenies toward self-incompatibility. However, pollinations are normally made with much more pollen than is necessary to fertilize all available ovules. This creates competition in favor of the fastest growing pollen types, eliminating the slow growing pollen tubes, including those with a tendency toward self-incompatibility. However, by using limited quantities of pollen, among other methods, it is possible to eliminate pollen tube growth competition, thereby allowing the preservation of alleles which tend toward self-incompatibility.

Once homozygosity occurs at a locus, it is never lost, as long as self- pollination continues. This is because, with selfing, there is no source of genetic variation available for such loci. Consequently continued selfing and appropriate selection will result in the accumulation of homozygous loci and the gradual reduction in self-compatibility. If selfing continues, and pollen tube growth competition is excluded, enough homozygous loci will be established to render the line self-incompatible. The line can then be used in the production of hybrid plants, especially crops.

Genetic Variations

Genetic variations may be introduced into a plant species using numerous methods available to the skilled artisan. For example, standard inbred lines can be emasculated by hand before pollen anthesis and then pollinated by another inbred line. Alternatively, they can be subjected to interspecific and intergeneric crosses including, as sources of genetic variation, taxa which are either self-compatible or self-incompatible. Alternatively, taxa can be hybridized by protoplast fusion and then regenerated. Other methods for generating the necessary genetic variation include treatment of genotypes with mutagenic agents chemical mutagens, such as, for example, diethyl sulfate, ethylene imine, ethly methanesulfonate, nitroso ethyl urea, and sodium azide; radiation such as x-rays, gamma rays, ultraviolent radiation. See for example, Maan, U.S. Pat. No. 4,143,486 which is incorporated herein by reference. Somaclonal variation which occurs in cell and callus cultures can also be used to generate the desired genetic variation. See for example, Evans et al., *Science*, 221 949–951 (1983); *Genetic Engineering of Plants*, National Academy Press, Washington, D.C., pp 33–39 (1984).

Inbreeding for Self-Incompatibility

After the genetic variation has been introduced, the heterozygous ($F_1$, $M_1$, etc.) individuals are brought into flower, the flowers are emasculated before pollen anthesis and, when stigmas are mature and receptive, they are self-pollinated.

An essential aspect of this self-pollination is that it must be accomplished in the nearly complete absence of pollen tube growth competition. Such competition creates selection in favor of rapidly growing pollen tubes. This competition is against the development of self incompatibility since the slowly growing pollen tubes include those which show tendencies toward self-incompatibility.

Pollen tube growth competition is eliminated by applying to stigmas, as a maximum, a number (or amount) of pollen grains which just suffices to produce a number of seeds equal to, or slightly smaller than, the number of seeds resulting from a standard pollination. A "standard" pollination is one in which the number of pollen grains applied greatly exceeds the number of ovules available for fertilization. In cases of single-seeded fruits, the number of pollen grains used in each pollination should be the minimum which will effect fertilization and seedset.

Pollinations employing limited quantities of pollen or employing other methods of reducing or eliminating pollen tube growth competition are hereafter referred to as "limited pollinations" or "limited selfings."

Other methods of reducing or eliminating pollen tube competition are:

1. Mix the pollen with an inert substance, e.g., talc, lycopodium spores, or nonviable pollen. This has the effect of diluting the amount of available viable pollen and thus reduces the numbers of viable pollen grains used in pollinations.

2. Shorten the styles before pollination. The longer the style, the greater is the opportunity for rapidly growing pollen tubes to surpass slower tubes. With short styles, pollen tube growth competition is drastically reduced. Shortening styles is easily accomplished in species such as *Zea mays* (corn) by cutting back the silks as much as possible (to <3 cm.). With other species, the style may be split longitudinally and pollen applied to the stylar interior. Finally, ovaries or placenta containing ovules may be cultured and pollinated on an artificial medium, thereby removing the styles totaly, see Titon and Russell, *Bioscience*, 34 239–242 (1984).

3. Select seeds from the stylar end of the fruit.

4. Disable the fastest growing pollen tubes by excising, irradiating, or by like means, that portion of the style in which these tubes but not slower growing tubes are located.

A fraction of the seeds which result from these limited selfings are planted and measured for their tendencies toward self-incompatability. Selected individuals are then subjected to limited selfing. The process is generally repeated for a total of about 6 generations or until self-incompatibility is attained.

In later generations of limited selfings, the optimal temperature for pollen tube growth in the style should be determined, and all subsequent pollinations should be made at this temperature. This is accomplished by growing the plants at various temperatures, and by direct as indirect observation methods determining the optimal temperature for pollen tube growth. This allows the investigator to identify those genotypes which, even at the optimal temperature for pollen tube growth, are unable to effect self-fertilization.

At the start of the selection process, all plants will be self-compatible. The method presented herein requires selecting for increased tendencies toward self-incompatibility, culminating in achieving full self-incompatibility. This requires some means of identifying and selecting individuals which exhibit a tendency toward self-incompatibility. Two general indications of tendencies toward self-incompatibility are:

1. Slower growth of pollen tubes on self styles than on non-self styles.
2. Reduced seed set after selfing than after crossing.

Both of these, as explained below, are measurable.

Before considering methods for measuring tendancies toward self-incompatibility, it is necessary to consider that either indicator of self-incompatibility may reflect the operation of several factors but only three of these factors must be considered in order to explain the experiment described below.

1. The pollen may be inherently weak or slow growing. This may be determined by measuring the ability of each pollen type to grow in several non-self styles.
2. The styles may be generally unfavorable for pollen tube growth. This may be determined by measuring the ability of each style type to support growth of several non-self pollen tube types.
3. True self-incompatibility, that is, the failure of otherwise fertile plants to set seeds after selfing. This may be determined by measuring the ability of self pollen to penetrate self styles, allowing for the general quality of the pollen and the style in non-self crosses (See Table I and Table II).

Measuring Tendencies Toward Self-Incompatibility:

In order to identify and to select for tendencies toward true self-incompatibility, it is necessary to distinquish the three above listed factors. Two methods for doing this are described herein as "direct" and "indirect" methods, as shown below.

Direct Method:

The direct method requires that the pollen tubes be seen within the style. This is easily accomplished by using any of several staining methods to clear the styles and to stain and observe pollen tubes within them. For example, Martin's technique of clearing in NaOH, staining in decolorized aniline blue, and, observation with fluorescent microsopy may be employed, see: Martin, F. W., *Stain Tech.*, 34 125–128 (1958).

The crosses represented in Table I are made, and when pollen tubes have, on the average, penetrated approximately ¼ to ¾ of the length of the style, pollinated flowers are collected and prepared for examination, for example, using Martin's technique. If the analysis indicates that an individual plant shows a significant tendency toward self-incompatibility, it is then included among those plants which will be subjected to further limited selfings and selection.

A tendency toward self-incompatibility may be expressed as slow or incomplete pollen tube growth in selfed styles. However, slow or incomplete pollen tube growth could also be the result of poor quality pollen or poor quality styles. The following diagram (Table I) indicates that pollinating the style of one genotype (A) with pollen from other genotypes (B) and (C) will test the quality of genotype (A) styles. Pollinating styles of genotype (B) and (C) with genotype (A) pollen, will test the quality of (A) pollen. Knowing the relative quality of (A) styles and (A) pollen will allow the prediction of the rate of (A) pollen tube growth in (A) styles. The extent to which the observed pollen tube growth rate is less than the predicted growth rate, indicates the tendency of genotype (A) toward self-incompatibility.

TABLE I

DIRECT OBSERVATION CROSSING DIAGRAM
(Factors listed in the crossing diagram indicate which parameters will be measured by each cross)

| Ovulate Parent | Pollen Parent | | |
|---|---|---|---|
| | A | B | C |
| A | Self-incompatibility (X) | Quality of "A" style | Quality of "A" style |
| B | Quality of "A" pollen | | |
| C | Quality of "A" pollen | | |

(X) True tendency toward self-incompatibility will be indicated by adjusting the observed self-incompatibility for influences of variation in the general quality of pollen and styles from line #"A".

Indirect Method:

The indirect method of determining the growth rate of pollen requires that the speed of self pollen tubes be compared to a standard tester pollen. Since this method depends on the number of fertilizations accomplished both by the self and by the tester pollen it actually reflects a combination of two indicators of self-incompatibility; pollen tube growth rate and seed set after selfing. In some cases, however, it gives specific indications of pollen tube growth rates.

The indirect method is most easily envisioned by considering the following table (II) in order to determine the degree of self-incompatibility in plant "A". The method requires the use of three other genetic lines, one, a standard tester line (T), which carries a dominant genetic marker, and two others, lines B and C. Lines A, B, and C are each homozygous recessive for the line T marker. To determine the degree of self-incompatibility in plant A, pollen from plant A is mixed with an approximately equal quantity of pollen from line T. This pollen mixture is then applied to stigmas of lines A, B, and C. As soon as the line T dominant marker is expressed in the resultant generation, the relative proportions of progeny from pollen types A and T are determined for each cross. Tendencies toward self-incompatibility will be expressed as the relative proportion of "A" progeny produced in each cross. For example, if the proportion of "A" progeny is significantly lower in pollinations to "A" stigmas than it is when "B" or "C" is the pistillate parent, then plant A will be considered to exhibit a significant tendency toward self-incompatibility. The greater the difference between the proportion of "A" progeny with "A" versus "B" or "C" as the pistillate parent, the greater will be the tendency toward self-incompatibility shown by "A". (See Table II).

TABLE II

INDIRECT OBSERVATION CROSSING DIAGRAM
Factors listed in the crossing diagram indicate which parameters will be measured by each cross.

| Ovulate Parent | Pollen Mixture Used A + T |
|---|---|
| A | Self-incompatibility (X) |
| B | Quality of "A" pollen |
| C | Quality of "A" pollen |

(X) The number of fertilizations accomplished by "A" pollen from the mixture (A + T) when applied to ovulate parents "B" and "C" will indicate both fraction and general quality of "A" pollen grains within the A + T pollen mixture. With that as a standard, we can predict that a comparable fraction of fertilizations accomplished by "A" pollen when the same mixture (A + T) is applied to "A" stigmas.
The degree of self-incompatibility in line "A" will be indicated by the extent to which "A" pollen within the A + T mixture accomplishes fewer fertilizations on "A" pistils than it does on "B" or "C" pistils (averaged).
The second indicator of self-incompatibility, reduced seed set after selfing, can be determined by comparing seed after self- and non-self-pollinations.

During the process of inbreeding with limited selfings, those skilled in the art will be able to identify individual plant lines which produce pollen that has a significantly better probability of effecting fertilization when applied to the stigma of another line than when used in self-pollination. Attention is concentrated on these lines, making a greater number of limited selfings on them.

The following example is provided to aid in the understanding of the present invention. Modifications and variations of the invention as described herein can be made by those artisans skilled in the art; and such modifications and/or variations are deemed to be within the scope of the appended claims.

EXAMPLE

A highly heterozygous plant is selfed with enough pollen to set fruit but not enough to result in pollen tube growth competition. The resulting seeds, for example $F_2$ seeds, are planted and, using either direct or indirect methods (which are explained above), the tendency toward self-incompatibility is measured within each of the 500 resulting plants.

The 200 $F_2$ plants exhibiting the greatest such tendencies are then self pollinated, again using limited pollination.

$F_3$ families of 20 or more individuals are raised from each of the 200 selected $F_2$ plants. Within each family, 10 individuals are measured for their tendency toward self-incompatibility.

Of the 200 $F_3$ families so measured the 50 families which exhibit the greatest such tendencies are selected and the tendency toward self-incompatibility is measured in another 10 individuals of each.

Within each of the 50 $F_3$ families which show the greatest average tendency toward self-incompatibility, the 5 most self-incompatible individuals, are self-pollinated again using limited pollination.

Any additional $F_3$ individuals which exhibit strong tendencies toward self-incompatibility, are self-pollinated (with limited pollen), even though these individuals were not part of a family selected for a strong tendency toward self-incompatibility.

Within each of the 250 (or more) $F_4$ families produced, measure the tendency toward self-incompatibility in 4 individuals is measured.

The process of screening for tendencies toward self-incompatibility, and subjecting individuals with the strongest such tendencies to limited selfing, is repeated until either complete self-incompatibility, or no-further response to selection is obtained. In those cases in which complete self-incompatibility is not obtained, individuals from different families showing the strongest such tendencies are intercrossed and the resulting progeny subjected to screening, limited selfing, etc., as described herein above.

Genetic segregants of these lines will ultimately include self-incompatible lines. Any two of these self-incompatible segregants can be used in the production of hybrid seeds.

Maintenance Of Self Incompatible Lines:

In order to produce hybrid plants, there must be some method of maintaining and increasing the parental lines. There are two general methods of accomplishing this:

1. Indirect Maintenance:

With this method, each parental line shall be obtained as the product of inbreeding a population called a "maintainer population." A maintainer population is one in which levels of heterozygosity are sufficiently high to allow self fertilization but sufficiently low so that inbreeding for one (or more) generations will generate a high degree of self-incompatibility. The self-incompatible plants so produced will constitute one parental line.

2. Direct Maintenance:

a. Sexual reproduction.

These methods require the circumvention of the self-incompatibility of highly inbred parental lines. In many species, e.g., corn, lily, etc., this may be done by shortening the styles. In others, aging or exposing either the plants or the styles, to high or low temperatures will overcome the self-incompatibility. Such treatments will allow the otherwise self-incompatible lines to be selfed and thereby increased.

b. Asexual reproduction.

Highly inbred parental lines may be maintained and multiplied either by traditional methods of cuttings, tillering, etc. or by production of callus, protoplast, etc. cultures which are well known in the art.

What is claimed is:

1. A method of achieving self-incompatibility in plants, said method comprising:
   (a) self-pollinating a highly heterozygous plant with sufficient pollen to set fruit but not result in pollen tube competition;
   (b) planting the seed resulting from the self-pollination and measuring each plants' tendency toward self-incompatibility;
   (c) self-pollinating those plants from step (b) exhibiting the highest degree of self-incompatibility;
   (d) repeating steps (b) and (c) with seeds from step (c) until a fully self-incompatable line is achieved.

2. The method of claim 1 which further comprises propagating said self-incompatible line of step (d) with pollen from a compatible variety of the same species to generate hybrid seeds.

3. The method of claim 2 which further comprises planting said hybrid seed to yield a hybrid crop plant.

4. The method of claim 3 wherein said hybrid crop plant is sugar beet.

5. The method of claim 1 wherein said hybrid crop plant is a cereal grain.

6. Hybrid seeds produced by the method of claim 2.

7. Hybrid crop plants produced by the method of claim 3.

8. A method of producing a self-incompatibile plant, said method comprising repeatedly inbreeding a self-compatible heterozygote and selecting from successive generations those plants exhibiting progessively stronger tendencies toward self-incompatibility and eliminating pollen tube growth competition in each of the successive inbreeding steps.

9. The method of claim 8 which further comprises inbreeding at temperature optimal for pollen tube growth through styles.

10. The method of claim 8 which further comprises cultivating said self-incompatible plant with a compatible variety of the same species to produce hybrid seeds.

11. The method of claim 10 which further comprises planting said hybrid seed to yield a hybrid crop plant.

12. Hybrid seeds produced by the method of claim 10.

13. The hybrid seed of claim 12 wherein said plant is sugar beets.

14. The hybrid seed of claim 12 wherein said plant is a cereal grain.

15. The hybrid crop plant produced by the method of claim 12.

16. The hybrid crop plant of claim 15 wherein said plant is sugar beet.

17. The hybrid crop plant of claim 15 wherein said plant is a cereal grain.

* * * * *